United States Patent
Reijmer et al.

(10) Patent No.: US 10,682,533 B2
(45) Date of Patent: Jun. 16, 2020

(54) MULTI-CAPSULE COMPOSITIONS

(71) Applicant: International Flavors & Fragrances Inc., New York, NY (US)

(72) Inventors: Henricus Gerardus Maria Reijmer, Hoevalaken (NL); Stephanus Cornelis Maria Otte, Heemstede (NL); Volkert Willem Alexander de Villeneuve, Voorburg (NL); Elizabeth Geertruida Maria Brundel, Nijkerk (NL)

(73) Assignee: International Flavors & Fragrances Inc., New York, NY (US)

( * ) Notice: Subject to any disclaimer, the term of this patent is extended or adjusted under 35 U.S.C. 154(b) by 26 days.

(21) Appl. No.: 15/422,506

(22) Filed: Feb. 2, 2017

(65) Prior Publication Data

US 2017/0145347 A1  May 25, 2017

Related U.S. Application Data

(62) Division of application No. 14/538,591, filed on Nov. 11, 2014, now Pat. No. 9,770,608.

(60) Provisional application No. 61/902,347, filed on Nov. 11, 2013.

(51) Int. Cl.

| | |
|---|---|
| *A61Q 13/00* | (2006.01) |
| *A61K 8/11* | (2006.01) |
| *A61K 8/72* | (2006.01) |
| *A61K 9/48* | (2006.01) |
| *A61Q 5/12* | (2006.01) |
| *C11D 3/00* | (2006.01) |
| *C11D 3/22* | (2006.01) |
| *C11D 3/37* | (2006.01) |
| *C11D 3/50* | (2006.01) |
| *C11D 11/00* | (2006.01) |
| *C11D 17/00* | (2006.01) |

(52) U.S. Cl.
CPC .............. *A61Q 13/00* (2013.01); *A61K 8/11* (2013.01); *A61K 8/72* (2013.01); *A61K 9/4891* (2013.01); *A61Q 5/12* (2013.01); *C11D 3/001* (2013.01); *C11D 3/222* (2013.01); *C11D 3/3723* (2013.01); *C11D 3/3769* (2013.01); *C11D 3/505* (2013.01); *C11D 11/0017* (2013.01); *C11D 17/0039* (2013.01); *A61K 2800/412* (2013.01); *A61K 2800/5922* (2013.01)

(58) Field of Classification Search
None
See application file for complete search history.

(56) References Cited

U.S. PATENT DOCUMENTS

| | | | | |
|---|---|---|---|---|
| 7,524,809 | B2* | 4/2009 | Trinh | C11D 3/001 510/101 |
| 2007/0078071 | A1* | 4/2007 | Lee | A61K 8/11 510/130 |
| 2009/0247449 | A1* | 10/2009 | Burdis | B01J 13/02 510/445 |
| 2012/0093899 | A1* | 4/2012 | Popplewell | B01J 13/02 424/401 |

FOREIGN PATENT DOCUMENTS

WO    WO-2011094681 A1 *   8/2011   ............... C11D 1/62

* cited by examiner

*Primary Examiner* — Bethany P Barham
*Assistant Examiner* — Barbara S Frazier
(74) *Attorney, Agent, or Firm* — Licata & Tyrrell P.C.

(57) ABSTRACT

A capsule delivery system. The system has a first capsule containing a first capsule wall encapsulating a first active material and a second capsule containing a second capsule wall encapsulating a second active material. The first and second capsules differ in their wall materials, amounts of wall materials, ratios of wall materials, core modifiers, scavengers, active materials, curing temperatures, heating rates, curing times, or a combination thereof. Also provided is a consumer product containing this capsule delivery system.

19 Claims, No Drawings

MULTI-CAPSULE COMPOSITIONS

CROSS-REFERENCE TO RELATED APPLICATIONS

This application claims priority to U.S. patent application Ser. No. 14/538,591, filed on Nov. 11, 2014, which claims priority to U.S. Patent Application Ser. No. 61/902,347 filed on Nov. 11, 2013. The contents of both applications are incorporated herein by reference in their entirety.

BACKGROUND OF THE INVENTION

Fragrance materials are used in numerous products to enhance the consumer's enjoyment of a product. Fragrance materials are added to consumer products such as laundry detergents, fabric softeners, soaps, detergents, personal care products, such as shampoos, body washes, deodorants and the like, as well as numerous other products.

To enhance the effectiveness of the fragrance materials for the user, various technologies have been employed to enhance the delivery of the fragrance materials at the desired time. One widely used technology is encapsulation of the fragrance material in a protective coating. Frequently the protective coating is a polymeric material. The polymeric material is used to protect the fragrance material from evaporation, reaction, oxidation or otherwise dissipating prior to use. For example, U.S. Pat. No. 4,081,384 discloses a softener or anti-stat core coated by a polycondensate suitable for use in a fabric conditioner. U.S. Pat. No. 5,112,688 discloses selected fragrance materials having the proper volatility to be coated by coacervation with microparticles in a wall that can be activated for use in fabric conditioning. U.S. Pat. No. 5,145,842 discloses a solid core of a fatty alcohol, ester, or other solid plus a fragrance coated by an aminoplast shell. U.S. Pat. No. 6,248,703 discloses various agents including fragrance in an aminoplast shell that is included in an extruded bar soap.

It is typically not desired that the encapsulated materials be released from the shell prematurely. Often, the capsule shell is somewhat permeable to the core contents when stored under certain conditions. This is particularly the case when many capsule types, such as those having aminoplast or cross-linked gelatin walls, are stored in aqueous bases, particularly those containing surfactants. In these cases, although the capsule shell is intact, the active material is diffused from the core over time in a leaching process. The overall leaching mechanism may be viewed as a diffusion process, with transfer occurring from the capsule core to the aqueous media, followed by transfer to or solubilization into the surfactant micelles or vesicles. With normal surfactant concentrations of between 1 and 50% in consumer products, as compared to active material levels of 0.3 to 1%, it is clear that the partitioning favors absorption by the surfactant over time.

There is also a need in the art to provide a microcapsule product with improved cost-in-use performance so that consumer product companies can use less microcapsule product to obtain equal or better performance/benefit.

SUMMARY OF THE INVENTION

One aspect of this invention related to a capsule delivery system composed of a first capsule containing a first capsule wall encapsulating a first active material and a second capsule containing a second capsule wall encapsulating a second active material (e.g., at a ratio of about 1:9 to about 9:1). The first and second capsules differ in their wall materials, amounts of wall materials, ratios of wall materials, core modifiers, scavengers, active materials, curing temperatures, heating rates, curing times, or a combination thereof.

The first and second active materials can be the same or different. In some embodiments, the first or second active material is a fragrance. In certain embodiments, the first or second active material contains a malodor counteractant, e.g., 1-cyclohexylethan-1-yl butyrate, 1-cyclohexylethan-1-yl acetate, 1-cyclohexylethan-1-ol, 1-(4'-methylethyl)cyclohexylethan-1-yl propionate, 2'-hydroxy-1'-ethyl(2-phenoxy)-acetate, and a combination thereof.

The first and second capsule walls can be formed of melamine-formaldehyde. In some embodiment, the first capsule is cured at or above about 120° C. for about 0.5 to about 5 hours and the second capsule is cured at about 70 to about 100° C. for about 0.5 to about 5 hours. In other embodiments, the first capsule contains a first fragrance as the first active material, in which the first fragrance has a plurality of fragrance ingredients and about 50 to 100 weight % of the ingredients have a saturated vapor pressure at 23° C. of about 0.01 mm Hg or greater, and the second capsule contains a second fragrance as the second active material, in which the second fragrance has a plurality of fragrance ingredients and about 20 to 100 weight % of the ingredient have a saturated vapor pressure at 23° C. of about 0.01 mm Hg or greater. The first capsule can be cured at or above about 100° C. for about 0.5 to about 2 hours and the second capsule can be cured at a temperature of less than about 100° C. for about 0.5 to about 2 hours. Alternatively, the first capsule is cured at a temperature of about 70 to about 130° C. for about 2 to about 4 hours and the second capsule is cured at a temperature of about 70 to about 130° C. for about 0.5 to about 1.5 hours.

The first and second capsule walls can be different. In some embodiment, the first capsule wall is formed of melamine-formaldehyde, and the second capsule wall is formed of polyurea or polyurethane. Typically, the first capsule wall is cured at or above about 70° C. (e.g., about 70 to about 130° C.) for about 0.5 to about 5 hours (e.g., about 0.5 to about 3.5 hours) and the second capsule is cured at or above about 50° C. (e.g., about 50 to about 110° C. for about 0.5 to about 2 hours.

In yet other embodiments, the first and second capsules are stable when added to a consumer product base (e.g., a fabric conditioner, detergent, fabric spray, personal wash product, home care product, liquid soap, shampoo, rinse-off conditioner, or leave-on conditioner) for more than four weeks or more than eight weeks when stored at 37° C. and have release profiles that do not substantially change after 4 weeks or 8 weeks in storage.

Any of the capsule delivery systems described above can further contain a starch particle having an active material pre-loaded on it. These systems can also contain one or more additional capsules, e.g., a third, a fourth, a fifth, a sixth, and a seventh capsules.

Another aspect of this invention relates to a consumer product base containing any of the capsule delivery systems described above. Exemplary consumer products include fabric conditioners, detergents, fabric sprays, personal wash products, home care products, liquid soaps, shampoos, rinse-off conditioners, and leave-on conditioners. When the consumer product is a fabric conditioner or detergent, the fabric conditioner contains about 1 to about 30 weight % (e.g., about 5 to about 10 weight %, about 8 to about 15 weight %, and about 10 to about 20 weight %) of a fabric conditioning active, and the detergent contains about 1 to 75 weight % (e.g., about 5 to about 50 weight % and about 15 to about 30 weight %).

DETAILED DESCRIPTION OF THE INVENTION

Capsules are conventionally cured at temperatures in the range of about 50 to about 85° C. Due to the nature of the polymers used to encapsulate the active materials and the volatile nature of fragrance components, which would be compromised under increased curing temperatures, it would not be expected that increasing the curing temperature would provide capsules with improved retention capabilities. However, a crosslinked network of polymers containing active materials cured at high temperatures and for periods of time greater than one hour can provide a microcapsule product capable of retaining a much wider range of active materials during storage in consumer product bases that contain surfactants, alcohols, volatile silicones and mixtures thereof than previously possible. For example, enhanced retention may be achieved with materials with lower c log P values. See US 2007/0138673. However, it has now been found that capsules cured at high temperatures do not have an overall desirable release profile, e.g., they lack a desirable release profile in each of the damp, pre-rub and post-rub stages of a model fabric conditioner.

Therefore, the present invention features a capsule delivery system composed of a combination of microcapsules that have one or more different characteristics, which result in desirable release profiles and/or stability. In particular, the system of the invention includes a combination of two or more types of microcapsules that differ in their wall materials, amounts of wall materials, ratios of wall materials, core modifiers, scavengers, active materials, cure temperatures, heating rates during the curing, curing times or a combination thereof. In some embodiments, the system is composed of two, three, four, five, six, seven or more different types of capsules that differ by one or more of the above-referenced characteristics. In particular embodiments, the system is composed of two types of microcapsules, described herein as a first capsule containing a first capsule wall encapsulating a first active material and a second capsule containing a second capsule wall encapsulating a second active material.

The terms "capsules," "microcapsules," and encapsulated materials" herein are used interchangeably.

In accordance with some embodiments, the two or more different types of capsules of the system have different wall characteristics, e.g., different wall materials, different amounts of wall materials, and/or different ratios of wall materials. By way of illustration, a first capsule can be composed of melamine-formaldehyde and a second capsule can be composed of urea-formaldehyde so that the first and second capsules have different wall materials. In another illustrative example, a first capsule can be composed of 10% co-polyacrylamide/acrylate and 6% methylated melamine crosslinker and a second capsule can be composed of 5% co-polyacrylamide/acrylate and 3% methylated melamine crosslinker so that the first and second capsules have different amounts of wall materials. As yet another illustrative example, a first capsule can be composed of 5% co-polyacrylamide/acrylate and 5% methylated melamine crosslinker and a second capsule can be composed of 5% co-polyacrylamide/acrylate and 3% methylated melamine crosslinker so that the first and second capsules have different ratios of wall materials.

Encapsulation of active materials such as fragrances is known in the art, see for example U.S. Pat. Nos. 2,800,457, 3,870,542, 3,516,941, 3,415,758, 3,041,288, 5,112,688, 6,329,057, 6,261,483, and 8,299,011. Another discussion of fragrance encapsulation is found in the Kirk-Othmer Encyclopedia.

Preferred encapsulating polymers include those formed from melamine-formaldehyde or urea-formaldehyde condensates, or co-polyacrylamide/acrylate with a methylated melamine crosslinker, as well as similar types of aminoplasts. Additionally, microcapsules made via the simple or complex coacervation of gelatin are also preferred for use with a coating. Microcapsules having shell walls composed of polyurethane, polyurea, polyamide, polyolefin, polysaccharide, protein, silicone, lipid, modified cellulose, gums, polyacrylate, polystyrene, polyester or any combination thereof are also functional.

A representative process used for aminoplast encapsulation is disclosed in U.S. Pat. No. 3,516,941 though it is recognized that many variations with regard to materials and process steps are possible. A representative process used for gelatin encapsulation is disclosed in U.S. Pat. No. 2,800,457 though it is recognized that many variations with regard to materials and process steps are possible. Both of these processes are discussed in the context of fragrance encapsulation for use in consumer products in U.S. Pat. Nos. 4,145,184 and 5,112,688, respectively.

Microcapsule formation using melamine-formaldehyde or urea-formaldehyde pre-condensates in combination with polymers containing substituted vinyl monomeric units having proton-donating functional group moieties (e.g. sulfonic acid groups or carboxylic acid anhydride groups) bonded thereto is disclosed in U.S. Pat. No. 4,406,816 (2-acrylamido-2-methyl-propane sulfonic acid groups), GB 2,062, 570 A (styrene sulfonic acid groups) and GB 2,006,709 A (carboxylic acid anhydride groups).

The cross-linkable acrylic acid polymer or co-polymer microcapsule shell wall precursor has a plurality of carboxylic acid moieties and is preferably one or a blend of an acrylic acid polymer; a methacrylic acid polymer; an acrylic acid-methacrylic acid co-polymer; an acrylamide-acrylic acid co-polymer; a methacrylamide-acrylic acid co-polymer; an acrylamide-methacrylic acid co-polymer; a methacrylamide-methacrylic acid co-polymer; a $C_1$-$C_4$ alkyl acrylate-acrylic acid co-polymer; a $C_1$-$C_4$ alkyl acrylate-methacrylic acid co-polymer; a $C_1$-$C_4$ alkyl methacrylate-acrylic acid co-polymer; a $C_1$-$C_4$ alkyl methacrylate-methacrylic acid co-polymer; a $C_1$-$C_4$ alkyl acrylate-acrylic acid-acrylamide co-polymer; a $C_1$-$C_4$ alkyl acrylate-methacrylic acid-acrylamide co-polymer; a $C_1$-$C_4$ alkyl methacrylate-acrylic acid-acrylamide co-polymer; a $C_1$-$C_4$ alkyl methacrylate-methacrylic acid-acrylamide co-polymer; a $C_1$-$C_4$ alkyl acrylate-acrylic acid-methacrylamide co-polymer; a $C_1$-$C_4$ alkyl acrylate-methacrylic acid-methacrylamide co-polymer; a $C_1$-$C_4$ alkyl methacrylate-acrylic acid-methacrylamide co-polymer; and a $C_1$-$C_4$ alkyl methacrylate-methacrylic acid-methacrylamide co-polymer; and more preferably, an acrylic acid-acrylamide copolymer.

When substituted or un-substituted acrylic acid co-polymers are employed in the practice of this invention, in the case of using a co-polymer having two different monomeric units, e.g., acrylamide monomeric units and acrylic acid monomeric units, the mole ratio of the first monomeric unit to the second monomeric unit is in the range of from about 1:9 to about 9:1, preferably from about 3:7 to about 7:3. In the case of using a co-polymer having three different monomeric units, e.g., ethyl methacrylate, acrylic acid and acrylamide, the mole ratio of the first monomeric unit to the second monomeric unit to the third monomeric unit is in the range of about 1:1:8 to about 8:8:1, preferably from about 3:3:7 to about 7:7:3.

The molecular weight range of the substituted or un-substituted acrylic acid polymers or co-polymers useful in the practice of this invention is from about 5,000 to about 1,000,000, preferably from about 10,000 to about 100,000. The substituted or un-substituted acrylic acid polymers or co-polymers useful in the practice of this invention may be branched, linear, star-shaped, dendritic-shaped or may be a block polymer or copolymer, or blends of any of the aforementioned polymers or copolymers.

Such substituted or un-substituted acrylic acid polymers or co-polymers may be prepared according to any processes known to those skilled in the art, for example, U.S. Pat. No. 6,545,084.

Urea-formaldehyde and melamine-formaldehyde pre-condensate microcapsule shell wall precursors are prepared by means of reacting urea or melamine with formaldehyde where the mole ratio of melamine or urea to formaldehyde is in the range of from about 10:1 to about 1:6, preferably from about 1:2 to about 1:5. For purposes of practicing the invention, the resulting material has a molecular weight in the range of from about 150 to about 3000. The resulting material may be used 'as-is' as a cross-linking agent for the aforementioned substituted or un-substituted acrylic acid polymer or copolymer or it may be further reacted with a $C_1$-$C_6$ alkanol, e.g., methanol, ethanol, 2-propanol, 3-propanol, 1-butanol, 1-pentanol or 1-hexanol, thereby forming a partial ether where the mole ratio of melamine or urea: formalhyde:alkanol is in the range of about 1:(0.1-6):(0.1-6). The resulting ether moiety-containing product may be used 'as-is' as a cross-linking agent for the aforementioned substituted or un-substituted acrylic acid polymer or copolymer, or it may be self-condensed to form dimers, trimers and/or tetramers which may also be used as cross-linking agents for the aforementioned substituted or un-substituted acrylic acid polymers or co-polymers. Methods for formation of such melamine-formaldehyde and urea-formaldehyde pre-condensates are set forth in U.S. Pat. Nos. 3,516,846, 6,261,483, and Lee, et al. (2002) *J. Microencapsulation* 19:559-569. Examples of urea-formaldehyde pre-condensates useful in the practice of the invention are URAC 180 and URAC 186 (Cytec Technology Corp., Wilmington, Del.). Examples of melamine-formaldehyde pre-condensates useful in the practice of our invention are CYMEL U-60, CYMEL U-64 and CYMEL U-65 (Cytec Technology Corp.). In the practice of this invention it is preferable to use as the precondensate for cross-linking the substituted or un-substituted acrylic acid polymer or co-polymer.

In practicing this invention, the range of mole ratios of urea-formaldehyde precondensate or melamine-formaldehyde pre-condensate:substituted or un-substituted acrylic acid polymer or co-polymer is in the range of from about 9:1 to about 1:9, preferably from about 5:1 to about 1:5 and most preferably from about 2:1 to about 1:2.

In another embodiment, microcapsules with polymer(s) composed of primary and/or secondary amine reactive groups or mixtures thereof and crosslinkers can be used, as disclosed in US 2006/0248665. The amine polymers can possess primary and/or secondary amine functionalities and can be of either natural or synthetic origin. Amine containing polymers of natural origin are typically proteins such as gelatin and albumen, as well as some polysaccharides. Synthetic amine polymers include various degrees of hydrolyzed polyvinyl formamides, polyvinylamines, polyallyl amines and other synthetic polymers with primary and secondary amine pendants. Examples of suitable amine polymers are the LUPAMIN series of polyvinyl formamides (available from BASF). The molecular weights of these materials can range from about 10,000 to about 1,000,000.

The polymers containing primary and/or secondary amines can be used with any of the following comonomers in any combination (i) vinyl and acrylic monomers having alkyl, aryl and silyl substituents; OH, COOH, SH, aldehyde, trimonium, sulfonate, $NH_2$, NHR substituents; or vinyl pyridine, vinyl pyridine-N-oxide, vinyl pyrrolidon; (ii) cationic monomers such as dialkyl dimethylammonium chloride, vinyl imidazolinium halides, methylated vinyl pyridine, cationic acrylamides and guanidine-based monomers; or (iii) N-vinyl formamide and any mixtures thereof. The ratio of amine monomer/total monomer ranges from about 0.01 to about 0.99, more preferred from about 0.1 to about 0.9.

In addition, instead of amine-containing polymers it is possible to utilize amine-generating polymers that can generate primary and secondary amines during the microcapsule formation process as disclosed in US 2006/0248665.

The crosslinkers can include aminoplasts, aldehydes such as formaldehyde and acetaldehyde, dialdehydes such as glutaraldehyde, epoxy, active oxygen such as ozone and OH radicals, poly-substituted carboxylic acids and derivatives such as acid chlorides, anyhydrides, isocyanates, diketones, halide-substituted, sulfonyl chloride-based organics, inorganic crosslinkers such as $Ca^{2+}$, organics capable of forming azo, azoxy and hydrazo bonds, lactones and lactams, thionyl chloride, phosgene, tannin/tannic acid, polyphenols and mixtures thereof. Furthermore, processes such as free radical and radiation crosslinking can be used according to the present invention. Examples of free radical crosslinkers are benzoyl peroxide, sodium persulfate, azoisobutylnitrile (AIBN) and mixtures thereof.

With respect to the crosslinker, wall properties are influenced by two factors, the degree of crosslinking and the hydrophobic or hydrophilic nature of the crosslinker. The quantity and reactivity of the crosslinker determine the degree of crosslinking. The degree of crosslinking influences the microcapsule wall permeability by forming a physical barrier towards diffusion. Walls made from crosslinkers possessing low-reactive groups will have smaller degrees of crosslinking than walls made from high-reactive crosslinkers. If a high degree of crosslinking is desired from a low-reactive crosslinker, more is added. If a low degree of crosslinking is desired from a high-reactive crosslinker, then less is added. The nature and quantity of the crosslinker can also influence the hydrophobicity/hydrophilicity of the wall. Some crosslinkers are more hydrophobic than others and these can be used to impart hydrophobic qualities to the wall, with the degree of hydrophobicity directly proportional to the quantity of crosslinker used.

Optimization of the degree of crosslinked network of the microcapsules can be reached by adjusting the amount of crosslinker used in combination with the curing temperatures, e.g., below, at or above about 100° C.

The degree of crosslinking and degree of hydrophobicity can result from a single crosslinker or a combination of crosslinkers. A crosslinker that is highly reactive and hydrophobic can be used to create microcapsule walls with a high degree of crosslinking and a hydrophobic nature. Single crosslinkers that possess both these qualities are limited and thus crosslinker blends can be employed to exploit these combinations. Crosslinkers possessing high reactivities but low hydrophobicities can be used in combination with a low reactive, high hydrophobicity crosslinker to yield walls with high degrees of crosslinking and high hydrophobicity. Suitable crosslinkers are disclosed in US 2006/0248665.

The molecular weight range of the substituted or un-substituted amine-containing polymers or co-polymers and mixtures thereof, useful in the practice of this invention is from about 1,000 to about 1,000,000, preferably from about 10,000 to about 500,000. The substituted or un-substituted amine-containing polymers or co-polymers useful in the practice of our invention may be branched, linear, star-shaped, graft, ladder, comb/brush, dendritic-shaped or may be a block polymer or copolymer, or blends of any of the aforementioned polymers or copolymers. Alternatively, these polymers may also possess thermotropic and/or lyotropic liquid crystalline properties.

Polyurea capsules can be prepared using multi-functional isocyanates and multi-functional amines. See WO 2004/054362; EP 0 148149; EP 0 017 409 B1; U.S. Pat. Nos. 4,417,916, 4,124,526, 4,285,720, 4,681,806, 5,583,090, 6,340,653 6,566,306, 6,730,635, 8,299,011, WO 90/08468, and WO 92/13450.

These isocyanates contain two or more isocyanate (—NCO) groups. Suitable isocyanates include, for example, 1,5-naphthylene diisocyanate, 4,4'-diphenylmethane diisocyanate (MDI), hydrogenated MDI (H12MDI), xylylene diisocyanate (XDI), tetramethylxylol diisocyanate (TMXDI), 4,4'-diphenyldimethylmethane diisocyanate, di- and tetraalkyldiphenylmethane diisocyanate, 4,4'-dibenzyl diisocyanate, 1,3-phenylene diisocyanate, 1,4-phenylene diisocyanate, the isomers of tolylene diisocyanate (TDI), optionally in a mixture, 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, 4,4'-diisocyanatophenylperfluoroethane, tetramethoxybutane 1,4-diisocyanate, butane 1,4-diisocyanate, hexane 1,6-diisocyanate (HDI), dicyclohexylmethane diisocyanate, cyclohexane 1,4-diisocyanate, ethylene diisocyanate, phthalic acid bisisocyanatoethyl ester, also polyisocyanates with reactive halogen atoms, such as 1-chloromethylphenyl 2,4-diisocyanate, 1-bromomethylphenyl 2,6-diisocyanate, and 3,3-bischloromethyl ether 4,4'-diphenyldiisocyanate. Sulfur-containing polyisocyanates are obtained, for example, by reacting hexamethylene diisocyanate with thiodiglycol or dihydroxydihexyl sulfide. Further suitable diisocyanates are trimethylhexamethylene diisocyanate, 1,4-diisocyanatobutane, 1,2-diisocyanatododecane and dimer fatty acid diisocyanate.

The multi-functional amines contain two or more amine groups including —NH$_2$ and —RNH, R being substituted and unsubstituted C$_1$-C$_{20}$ alkyl, C$_1$-C$_{20}$ heteroalkyl, C$_1$-C$_{20}$ cycloalkyl, 3- to 8-membered heterocycloalkyl, aryl, and heteroaryl.

Water soluble diamines are one class of useful amines to form a polyurea capsule wall. One class of exemplary amines is of the type:

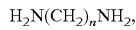

where n is ≥1. When n is 1, the amine is methylenediamine. When n is 2, the amine is ethylenediamine and so on. Suitable amines of this type include, but are not limited to, ethylenediamine, 1,3-diaminopropane, 1,4-diaminobutane, hexanethylene diamine, hexamethylene diamine, and pentaethylenehexamine. In particular embodiments of this invention, the preferred n is 6, where the amine is a hexamethylene diamine.

Amines that have a functionality greater than 2, but less than 3 and which may provide a degree of cross linking in the shell wall are also useful. Exemplary amines of this class are polyalykylene polyamines of the type:

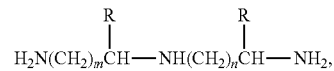

where R equals hydrogen or —CH$_3$, m is 1-5 and n is 1-5, e.g., diethylene triamine, triethylene tetraamine and the like. Exemplary amines of this type include, but are not limited to diethylenetriamine, bis(3-aminopropyl)amine, bis(hexamethylene)triamine.

Another class of amine that can be used in the invention is polyetheramines. They contain primary amino groups attached to the end of a polyether backbone. The polyether backbone is normally based on either propylene oxide (PO), ethylene oxide (EO), or mixed PO/EO. The ether amine can be monoamine, diamine, or triamine, based on this core structure. An example is:

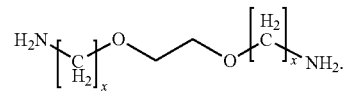

Exemplary polyetheramines include 2,2'-ethylenedioxy)bis(ethylamine) and 4,7,10-trioxa-1,13-tridecanediamine.

Other suitable amines include, but are not limited to, tris(2-aminoethyl)amine, triethylenetetramine, N,N'-bis(3-aminopropyl)-1,3-propanediamine, tetraethylene pentamine, 1,2-diaminopropane, N,N,N',N'-tetrakis(2-hydroxyethyl)ethylene diamine, N,N,N',N'-tetrakis(2-hydroxypropyl)ethylene diamine, branched polyethylenimine, 2,4-diamino-6-hydroxypyrimidine and 2,4,6-triaminopyrimidine.

Amphoteric amines, i.e., amines that can react as an acid as well as a base, are another class of amines of use in this invention. Examples of amphoteric amines include proteins and amino acids such as gelatin, L-lysine, L-arginine, L-lysine monohydrochloride, arginine monohydrochloride and omithine monohydrochloride.

Guanidine amines and guanidine salts are yet another class of amines of use in this invention. Exemplary guanidine amines and guanidine salts include, but are not limited to, 1,3-diaminoguanidine monohydrochloride, 1,1-dimethylbiguanide hydrochloride, guanidine carbonate and guanidine hydrochloride.

Other suitable amines include those commercially available such as JEFFAMINE EDR-148 (where x=2), JEFFAMINE EDR-176 (where x=3) (from Huntsman). Other polyether amines include the JEFFAMINE ED Series, and JEFFAMINE TRIAMINES.

The preparation of polyurethane capsules can be carried out by reacting one or more of the above-referenced isocyanates with alcohols including diols or polyols in the presence of a catalyst. Diols or polyols of use in the present invention have a molecular weight in the range of 200-2000. Exemplary diols include, but are not limited to, ethylene glycol, diethylene glycol, propylene glycol, 1,4-butane diol, 1,4-hexane diol, dipropylene glycol, cyclohexyl 1,4-dimethanol, and 1,8-octane diol. Exemplary polyols include, but are not limited to, poly (ethylene glycols), poly (propylene glycols), and poly (tetramethylene glycols). Alcohols having at least two nucleophilic centers are also useful, e.g., hexylene glycol, pentaerythritol, glucose, sorbitol, and 2-aminoethanol.

Catalysts suitable for use in the invention are amino or organometallic compounds and include, for example, 1,4-diazabicyclo[2.2.2]octane (e.g., DABCO, Air Products, Allentown, Pa.), N,N-dimethylaminoethanol, N,N-dimethylcyclohexylamine, bis-(2-dimethylaminoethyl) ether, N,N dimethylacetylamine, stannous octoate and dibutyltin dilaurate.

Table 1 below lists typical cross-liners useful for preparing the polyurea and polyurethane walls.

TABLE 1

| Active Hydrogen Compound | Typical Structure | Rel Rxn Rate w/ p-MDI @ 25° C. |
|---|---|---|
| 1° Aliphatic Amine | R—NH$_2$ | 100,000 |
| 2° Aliphatic Amine | R$_1$R$_2$NH | 20,000-50,000 |
| 1° Aromatic Amine | Ar—NH$_2$ | 200-300 |
| 1° Hydroxyl | R—CH$_2$—OH | 100 |
| Water | H—O—H | 100 |
| 2° Aromatic Amine | Ar—NH—R or Ar—NH—Ar' | 100 |
| Carboxylic Acid | R—COOH | 40 |
| 2° Hydroxyl | RR'CH—OH | 30 |
| Ureas | R—NH—C(O)—NH—R' | 15 |
| 3° Hydroxyl | R$_3$C—OH | 0.5 |
| Urethanes | R—NH—C(O)—O—R' | 0.3 |
| Amide | RC(O)—NH$_2$ | 0.1 |

Starch particles pre-loaded with a fragrance can also be included in the capsule delivery system of this invention. Examples of these starch particles can be found in Europe Patent 2606112 and U.S. Pat. No. 7,585,824. Suitable starch particles include those formed of porous starches, modified starches, carboxyalkyl starches, and cationically modified starches. These starches may have a molecular weight of about 100,000 to about 500,000,000 (e.g., about 200,000 to about 10,000,000 and about 250,000 to about 5,000,000). The weight ratio of the starch and the active material typically is about 1:25 to about 1:1 (e.g., about 1:10 to about 4:96). The weight ratio between the capsules and the starch particles can be about 1:20 to about 20:1 (e.g., about 1:5 to about 5:1).

The diameter of any of the microcapsules or particles described above can vary from about 10 nanometers to about 1000 microns, preferably from about 50 nanometers to about 100 microns and most preferably from about 1 to about 15 microns. The microcapsule distribution can be narrow, broad, or multi-modal. Each modal of the multi-modal distributions may be composed of different types of microcapsule chemistries.

In accordance with other embodiments, the two or more different types of capsules of the system have the same or different core characteristics, i.e., different active materials; different core modifiers such as solvents, emulsifiers and surfactants; and/or different scavengers. By way of illustration, a first capsule can contain of a combination of cinnamyl acetate and cinnamyl cinnamate and a second capsule can contain vanilla so that the first and second capsules have different core active materials.

The active material suitable for use in the present invention can be a wide variety of materials in which one would want to deliver in a controlled-release manner onto the surfaces being treated with the present compositions or into the environment surrounding the surfaces. Non-limiting examples of active materials include perfumes, flavoring agents, fungicide, brighteners, antistatic agents, wrinkle control agents, fabric softener actives, hard surface cleaning actives, skin and/or hair conditioning agents, malodour counteractants, antimicrobial actives, UV protection agents, insect repellents, animal/vermin repellants, flame retardants, and the like.

In a preferred embodiment, the active material is a fragrance, in which case the microcapsules containing fragrance provide a controlled-release scent onto the surface being treated or into the environment surrounding the surface. In this case, the fragrance can be composed of a number of fragrance raw materials known in the art, such as essential oils, botanical extracts, synthetic fragrance materials, and the like.

In general, the active material is contained in the microcapsules at a level of from about 1% to about 99% (e.g., about 10% to about 95%, about 30% to about 90%, and about 10 to about 50%) by weight of the total microcapsules. The weight of the total microcapsule particles includes the weight of the shell of the microcapsule plus the weight of the material inside the microcapsule.

The fragrances suitable for use in this invention include without limitation, any combination of fragrance, essential oil, plant extract or mixture thereof that is compatible with, and capable of being encapsulated by a polymer.

Many types of fragrances can be employed in the present invention, the only limitation being the compatibility and ability to be encapsulated by the polymer being employed, and compatibility with the encapsulation process used. Suitable fragrances include but are not limited to fruits such as almond, apple, cherry, grape, pear, pineapple, orange, strawberry, raspberry; musk, flower scents such as lavender-like, rose-like, iris-like, and carnation-like. Other pleasant scents include herbal scents such as rosemary, thyme, and sage; and woodland scents derived from pine, spruce and other forest smells. Fragrances may also be derived from various oils, such as essential oils, or from plant materials such as peppermint, spearmint and the like. Other familiar and popular smells can also be employed such as baby powder, popcorn, pizza, cotton candy and the like in the present invention.

A list of suitable fragrances is provided in U.S. Pat. Nos. 4,534,891, 5,112,688 and 5,145,842. Another source of suitable fragrances is found in Perfumes Cosmetics and Soaps, Second Edition, edited by W. A. Poucher, 1959. Among the fragrances provided in this treatise are acacia, cassie, chypre, cylamen, fern, gardenia, hawthorn, heliotrope, honeysuckle, hyacinth, jasmine, lilac, lily, magnolia, mimosa, narcissus, freshly-cut hay, orange blossom, orchids, reseda, sweet pea, trefle, tuberose, vanilla, violet, wallflower, and the like.

Furthermore, it is known in the art that the fragrance materials with lower log P or C log P (these terms will be used interchangeably from this point forward) exhibit higher aqueous solubility. Thus, when these materials are in the core of a microcapsule with a hydrated wall which is placed in an aqueous consumer product, they will have a greater tendency to diffuse into the surfactant-containing base if the shell wall is permeable to the fragrance materials.

As disclosed in U.S. Pat. No. 7,491,687, the log P of many perfume ingredients has been reported, for example, the Ponoma92 database, available from Daylight Chemical Information Systems, Inc. (Daylight CIS, Irvine, Calif.). The values are most conveniently calculated using C log P program also available from Daylight CIS. The program also lists experimentally determined log P values when available from the Pomona database. The calculated log P (C log P) is normally determined by the fragment approach (Hansch &

Leo (1990) in *Comprehensive Medicinal Chemistry*, Vol. 4, Hansch, et al. Editors, p. 295, Pergamon Press). This approach is based upon the chemical structure of the fragrance ingredient and takes into account the numbers and types of atoms, the atom connectivity and chemical bonding. The C log P values which are most reliable and widely used estimates for this physiochemical property can be used instead of the experimental log P values useful in the present invention. Further information regarding C log P and log P values can be found in U.S. Pat. No. 5,500,138.

The following fragrance ingredients provided in Table 1 are among those suitable for inclusion within the microcapsules of the present invention.

TABLE 1

| PERFUME INGREDIENTS | CLOGP |
|---|---|
| Allyl amyl glycolate | 2.72 |
| Allyl cyclohexane propionate | 3.94 |
| Ambrettolide | 6.26 |
| Iso-amyl acetate | 2.20 |
| Amyl benzoate | 3.42 |
| Amyl cinnamate | 3.77 |
| Amyl cinnamic aldehyde | 4.32 |
| Amyl cinnamic aldehyde dimethyl acetal | 4.03 |
| Iso-amyl salicylate | 4.60 |
| AURANTIOL (Hydroxycitronellal-methylanthranilate) | 4.22 |
| Benzyl salicylate | 4.38 |
| Butyl cyclohexanone | 2.84 |
| Para-tert-Butyl cyclohexyl acetate | 4.02 |
| Iso-butyl quinoline | 4.19 |
| Iso-butyl thiazole | 2.94 |
| Beta-Caryophyllene | 6.33 |
| Cadinene | 7.35 |
| Carvone | 2.27 |
| Cedrol | 4.53 |
| Cedryl acetate | 5.44 |
| Cedryl formate | 5.07 |
| Cinnamyl acetate | 2.39 |
| Cinnamyl cinnamate | 5.48 |
| Cyclohexyl salicylate | 5.27 |
| Cyclamen aldehyde | 3.68 |
| Cyclacet | 2.97 |
| Dihydro carvone | 2.41 |
| Diphenyl methane | 4.06 |
| Diphenyl oxide | 4.24 |
| Dodecalactone | 4.36 |
| ISO E SUPER 1-(1,2,3,4,5,6,7,8-Octahydro-2,3,8,8-tetramethyl-2-naphthalenyl)-ethanone) | 3.46 |
| Ethylene brassylate | 4.55 |
| Ethyl-2-methyl butyrate | 2.11 |
| Ethyl amyl ketone | 2.46 |
| Ethyl cinnamate | 2.85 |
| Ethyl undecylenate | 4.89 |
| EXALTOLIDE (15-Hydroxyentadecanlioc acid, lactone) | 5.35 |
| GALAXOLIDE (1,3,4,6,7,8-Hexahydro-4,6,6,7,8,8-hexamethylcyclopenta-gamma-2-benzopyran) | 5.48 |
| Geranyl anthranilate | 4.22 |
| Geranyl phenyl acetate | 5.23 |
| Hedione | 2.53 |
| Hexadecanolide | 6.81 |
| Hexenyl salicylate | 4.72 |
| Hexyl cinnamic aldehyde | 4.90 |
| Hexyl salicylate | 4.91 |
| Alpha-Irone | 3.82 |
| Liffarome | 2.23 |
| LILIAL (para-tertiary-butyl-alpha-methyl hydrocinnamic aldehyde | 3.86 |
| Linalyl benzoate | 5.23 |
| Lyral | 2.08 |
| Manzanate | 2.65 |
| Methyl caproate | 2.33 |
| Methyl dihydrojasmone | 4.84 |
| Gamma-n-Methyl ionone | 4.31 |
| Musk indanone | 5.46 |
| Musk tibetine | 3.83 |
| Oxahexadecanolide-10 | 4.34 |

TABLE 1-continued

| PERFUME INGREDIENTS | CLOGP |
|---|---|
| Oxahexadecanolide-11 | 4.34 |
| Patchouli alcohol | 4.53 |
| PHANTOLIDE (5-Acetyl-1,1,2,3,3,6-hexamethyl indan) | 5.98 |
| Phenyl ethyl benzoate | 4.21 |
| Phenylethylphenylacetate | 3.77 |
| Phenyl heptanol | 3.48 |
| Resetone | 2.59 |
| Alpha-Santalol | 3.80 |
| Styrallyl acetate | 2.05 |
| Thibetolide (15-Hydroxypentadecanoic acid, lactone) | 6.25 |
| Triplal | 2.34 |
| Delta-Undecalactone | 3.83 |
| Gamma-Undecalactone | 4.14 |
| Vetiveryl acetate | 4.88 |
| Ylangene | 6.27 |

In order to provide the highest fragrance impact from the fragrance encapsulated microcapsules deposited on the various substrates referenced above, it is preferred that materials with a high odor-activity be used. Materials with high odor-activity can be detected by sensory receptors at low concentrations in air, thus providing high fragrance perception from low levels of deposited microcapsules. This property must be balanced with the volatility as described above. Some of the principles mentioned above are disclosed in U.S. Pat. No. 5,112,688.

In embodiments pertaining to high temperature cured microcapsules described herein, a wider range of clog P materials may be employed because of the improved stability of the microcapsules. Accordingly, the core active material may have at least 60 weight % of materials with C log P greater than 2, preferably greater than 80 weight % with a C log P greater than 2.5 and more preferably greater than 80 weight % of materials with C log P greater than 3. In another embodiment, high stability microcapsules may also allow up to 100% retention of active material with log P equal to or less than 2 to be effectively encapsulated.

In certain embodiments of this invention, the first and second capsules have different amounts of fragrances with particular vapor pressures. In specific embodiments, the first capsule contains a fragrance, wherein about 50 to about 100 weight % of the fragrance, more preferably about 60 to about 100 weight % of the fragrance and most preferably about 70 to about 90 weight % of the fragrance has a saturated vapor pressure at 23° C. of about 0.01 mm Hg or greater, and the second capsule contains a fragrance, wherein about 20 to about 100 weight % of the fragrance, more preferably about 30 to about 80 weight % of the fragrance and even more preferably about 40 to about 60 weight % of the fragrance has a saturated vapor pressure at 23° C. of greater than or equal to about 0.01 mm Hg. In particular, the first capsule contains a fragrance, wherein about 50 to about 100 weight % of the fragrance, more preferably about 60 to about 100 weight % of the fragrance and most preferably about 70 to about 90 weight % of the fragrance has a saturated vapor pressure at 23° C. of greater than or equal to about 0.01 mm Hg and the capsule is cured at a temperature at or above 100° C. for at least 2 hours, and the second capsule contains a fragrance, wherein about 20 to about 100 weight % of the fragrance, more preferably about 30 and about 80 weight % of the fragrance and even more preferably about 40 to about 60 weight % of the fragrance has a saturated vapor pressure at 23° C. of greater than or equal to about 0.01 mm Hg and the capsule is cured at a temperature of less than 100° C. for less than 2 hours. The determination of saturated vapor pressure of fragrances can be carried out by conventional methods. See, e.g., Rudolfi et al. (1986) *J. Chromatograph. A* 365:413-415; Friberg & Yin (1999) *J. Disp. Sci. Technol.* 20:395-414.

Those with skill in the art appreciate that fragrance formulations are frequently complex mixtures of many fragrance ingredients. A perfumer commonly has several thousand fragrance chemicals to work from. Those with skill in the art appreciate that the each capsule of the first or second capsule may contain a single ingredient, but it is much more likely that the capsules will include at least eight or more fragrance chemicals, more likely to contain twelve or more and often twenty or more fragrance chemicals. The present invention also contemplates the use of complex fragrance formulations containing fifty or more fragrance chemicals, seventy five or more or even a hundred or more fragrance chemicals in a fragrance formulation.

The level of fragrance in a microcapsule of this invention varies from about 5 to about 95 weight %, preferably from about 40 to about 95 weight % and most preferably from about 50 to about 90 weight %. In addition to the fragrance, other materials can be used in conjunction with the fragrance and are understood to be included.

The present active material may further include one or more malodor counteractants at a level preferably less than about 70 weight % of the composition (e.g., about 0.1 to about 50 weight % and about 0.5 to about 5 weight %). The malodor counteractant composition serves to reduce or remove malodor from the surfaces or objects being treated with the present compositions. The malodor counteractant composition is preferably selected from uncomplexed cyclodextrin, odor blockers, reactive aldehydes, flavanoids, zeolites, activated carbon, and mixtures thereof. Compositions herein that include odor control agents can be used in methods to reduce or remove malodor from surfaces treated with the compositions.

Specific examples of malodor counteractant composition components useful in the microcapsules herein include, but are not limited to, malodor counteractant components such as 1-cyclohexylethan-1-yl butyrate, 1-cyclohexylethan-1-yl acetate, 1-cyclohexylethan-1-ol, 1-(4'-methylethyl)cyclohexylethan-1-yl propionate, and 2'-hydroxy-1'-ethyl(2-phenoxy)acetate, each of which compound is marketed under the trademark VEILEX by International Flavors & Fragrances Inc. (New York, N.Y.); and malodor counteractant components such as those disclosed in U.S. Pat. No. 6,379,658, which include β-naphthyl methyl ether, β-naphthyl ketone, benzyl acetone, mixture of hexahydro-4,7-methanoinden-5-yl propionate and hexahydro-4,7-methanoinden-6-yl propionate, 4-(2,6,6-trimethyl-2-cyclohexen-1-yl)-3-methyl-3-buten-2-one, 3,7-dimethyl-2,6-nonadien-1-nitrile, dodecahydro-3a,6,6,9a-tetramethyl naphtho(2,1-b)furan, ethylene glycol cyclic ester of n-dodecanedioic acid, 1-cyclohexadecen-6-one; 1-cycloheptadecen-10-one, and corn mint oil.

In addition to the fragrance materials and malodor counteractants, the present invention contemplates the incorporation of solvent materials into one or more of the microcapsules. The solvent materials are hydrophobic materials that are miscible in fragrance materials. The solvent materials serve to increase the compatibility of various active materials, increase the overall hydrophobicity of the blend, influence the vapor pressure of active materials, or serve to structure the blend. Suitable solvents are those having reasonable affinity for the fragrance chemicals and a C log P greater than about 2.5, preferably greater than about 3.5 and most preferably greater than about 5.5. Suitable solvent materials include, but are not limited to triglyceride oil, mono and diglycerides, mineral oil, silicone oil, diethyl phthalate, polyalpha olefins, castor oil and isopropyl myristate. In a preferred embodiment the solvent materials are combined with fragrance materials that have C log P values as set forth above. It should be noted that selecting a solvent and fragrance with high affinity for each other will result in the most pronounced improvement in stability. Appropriate solvents include, but are not limited to, mono-, di- and tri-esters, and mixtures thereof, or fatty acids and glycerine, wherein the fatty acid chain can range from $C_4$-$C_{26}$ and the fatty acid chain can have any level of unsaturation. For instance capric/caprylic triglyceride known as NEOBEE M5 (Stepan Corporation) is a suitable solvent. Other suitable examples are the CAPMUL series by Abitec Corporation. For instance, CAPMUL MCM. Additional solvents include, isopropyl myristate; fatty acid esters of polyglycerol oligomers, e.g., R2CO—[OCH$_2$—CH(OCOR1)-CH$_2$O—]$_n$, where R1 and R2 can be H or $C_4$-$C_{26}$ aliphatic chains, or mixtures thereof, and n ranges between about 2 and about 50, preferably about 2 and about 30; nonionic fatty alcohol alkoxylates like the NEODOL surfactants by BASF, the dobanol surfactants by Shell Corporation or the BIO-SOFT surfactants by Stepan, wherein the alkoxy group is ethoxy, propoxy, butoxy, or mixtures thereof and said surfactants can be end-capped with methyl groups in order to increase their hydrophobicity; di- and tri-fatty acid chain containing nonionic, anionic and cationic surfactants, and mixtures thereof; fatty acid esters of polyethylene glycol, polypropylene glycol, and polybutylene glycol, or mixtures thereof; polyalphaolefins such as the EXXONMOBIL PURESYM PAO line; esters such as the EXXONMOBIL PURESYN esters; mineral oil; silicone oils such polydimethyl siloxane and polydimethylcyclosiloxane; diethyl phthalate; di-octyl adipate and di-isodecyl adipate.

While no solvent is needed in the core, it is preferable that the level of solvent in the core of the microcapsule product should be less than about 80 weight %, preferably less than about 50 weight % and more preferably 0 to about 20 weight %. In addition to the solvent it is preferred that higher C log P fragrance materials are employed. It is preferred that greater than about 25 weight %, preferably greater than about 50 weight % and more preferably greater than about 90 weight % of the fragrance chemicals have C log P values between about 2 and about 7, preferably between about 2 and about 6 and more preferably between about 2 and about 5. Those with skill in the art will appreciate that many formulations can be created employing various solvents and fragrance chemicals. The use of relatively low to intermediate C log P fragrance chemicals will result in a fragrance that can be encapsulated, provided it is sufficiently water-insoluble, deliver ingredients onto critical consumer stages such as damp and dry fabric that would normally have evaporated or dissolved in water during the wash. Whilst high log p materials have excellent encapsulation properties they are generally well delivered from a regular (non-encapsulated) fragrance in a consumer product. Such fragrance chemicals would generally only need encapsulation for overall fragrance character purposes, very long-lasting fragrance delivery, or overcoming incompatibility with the consumer product, e.g., fragrance materials that would otherwise be instable, cause thickening or discoloration of the product or otherwise negatively affect desired consumer product properties.

A common feature of many encapsulation processes is that they require the fragrance material to be encapsulated to be dispersed in aqueous solutions of polymers, pre-condensates, surfactants, scavengers and the like prior to formation of the microcapsule walls. In one embodiment, the capsules of the system of this invention have different scavengers, in particular formaldehyde scavengers. According to this embodiment, the formaldehyde scavenger can be used from effective trace amounts up to 100 times (i.e., 100×) the stoichiometric amount. The stoichiometric amount is the amount of scavenger required to theoretically bind to or react with all the formaldehyde added in the form of an aminoplast crosslinker (bound and free formaldehyde). This amount of scavenger can be added either to the slurry or afterward to the final product formulation. For instance, an unscavenged slurry can be added to the formulation, followed by a certain amount of scavenger.

The particular quantity of a formaldehyde-based crosslinker that is used to create the capsule slurry contains a percentage of free formaldehyde and bound formaldehyde. The total combined moles of free and bound formaldehyde will determine the amount of moles of scavenger that is needed to react with all the formaldehyde. To drive this reaction to completion, about a 10× (i.e., 10 times) molar excess of scavenger is used, preferably about a 5× molar excess of scavenger. By moles here is meant moles of scavenging groups. Therefore, if the scavenger molecule is multifunctional (i.e., polymeric) less moles of this molecule needs to be added. This is the maximum level of scavenger needed based on the amount of crosslinker used.

The minimum level of scavenger required is that amount that scavenges only the free formaldehyde in the slurry. This level is determined analytically. The minimum amount of moles of scavenger required is equal to the moles of measured formaldehyde (1:1). Exemplary formaldehyde scavengers include β-dicarbonyl compounds; mono or di-amide scavengers; amines that form imines by reaction with formaldehyde; and formaldehyde reducers and sulfur containing compounds, such as those disclosed in US 2009/0258042.

The β-dicarbonyl compounds of the present invention have an acidic hydrogen giving rise to a nucleophilic atom that can react with formaldehyde. Specific examples of β-dicarbonyl compounds include, but are not limited to, acetoacetamide (BKB; Eastman), ethyl acetoacetate (EAA; Eastman), N,N-dimethyleneacetamide (DMAA; Eastman), acetoacetone, dimethyl-1,3-acetonedicarboxylate, 1,3-acetonedicarboxylic acid, malonic acid, resorcinol, 1,3-cyclohexadione, barbituric acid, 5,5-dimethyl-1,3-cyclohexanedione (dimedone), 2,2-dimethyl-1,3-dioxane-4,6-dione (Meldrum's acid), salicylic acid, methyl acetoacetate (MAA; Eastman), ethyl-2-methyl acetoacetate, 3-methylacetoacetone, dimethyl malonate, diethyl malonate, 1,3-dimethyl barbituric acid, resorcinol, phloroglucinol, orcinol, 2,4-dihydroxy benzoic acid, 3,5-dihydroxy benzoic acid, malonamide and 3-dicarbonyl scavengers listed in U.S. Pat. Nos. 5,194,674 and 5,446,195, as well as in Tomasino, et al. (1984) Textile Chemist and Colorist Vol. 16, No. 12.

Examples of the preferred effective mono- and di-amide scavengers are urea, ethylene urea, propylene urea, epsilon-caprolactam, glycouril, hydantoin, 2-oxazolidinone, 2-pyrrolidinone, uracil, barbituric acid, thymine, uric acid, allantoin, polyamides, 4,5-dihydroxyethylene urea, monomethylol-4-hydroxy-4-methoxy-5,5-dimethyl propylurea, nylon 2-hydroxyethyl ethylene urea (SR-511, SR-512; Sartomer), 2-hydroxyethyl urea (HYDROVANCE; National Starch), L-citrulline, biotin, N-methyl urea, N-ethyl urea, N-butyl urea, N-phenyl urea, 4,5-dimethoxy ethylene urea and succinimide.

Amines contemplated by this invention include, but are not limited to, poly(vinyl amine) (LUPAMIN; BASF), arginine, lysine, asparagines, proline, tryptophan, 2-amino-2-methyl-1-propanol (AMP); proteins such as casein, gelatin, collagen, whey protein, soy protein, and albumin; melamine, benzoguanamine, 4-aminobenzoic acid (PABA), 3-aminobenzoic acid, 2-aminobenzoic acid (anthranilic acid), 2-aminophenol, 3-aminophenol, 4-aminophenol, creatine, 4-aminosalicylic acid, 5-aminosalicylic acid, methyl anthranilate, methoxylamine HCl, anthranilamide, 4-aminobenzamide, p-toluidine, p-anisidine, sulfanilic acid, sulfanilamide, methyl-4-aminobenzoate, ethyl-4-aminobenzoate (benzocain), beta-diethylaminoethyl-4-aminobenzoate (procain), 4-aminobenzamide, 3,5-diaminobenzoic acid and 2,4-diaminophenol. Other amines as disclosed in US 2006/0248665 and U.S. Pat. No. 6,261,483, and those mentioned in Tomasino, et al. (1984) Textile Chemist and Colorist Vol. 16, No. 12, are also contemplated by the present invention. Hydrazines such as 2,4-dinitrophenylhydrazine can also react with formaldehyde by the first method to give hydrazones. The reaction is pH-dependent and reversible. Other preferred amines can be selected from a non-limiting list of 1,2-phenylenediamine, 1,3-phenylenediamine, and 1,4-phenylenediamine. In addition, aromatic amines, triamines, and aliphatic polyamine may also be used. Examples of these amines may include, but are not limited to, aniline, hexamethylenediamine, bis-hexamethylenetriamine, triethylaminetriamine, poly(propyleneoxide)triamine, and poly(propyleneglycol)diamines.

According to one embodiment of the invention, optional core modifiers may be added to the capsule slurry. For example, a non-confined unencapsulated active material from about 0.01 weight % to about 50 weight %, more preferably from about 5 weight % to about 40 weight % can be included. A capsule deposition aid (e.g., cationic starches such as Hi-CAT CWS42, cationic guars such as Jaguar C-162, cationic amino resins, cationic urea resins, hydrophobic quaternary amines, and the like) from about 0.01 weight % to about 25 weight %, and preferably from about 5 weight % to about 20 weight % can be included. Optionally, an emulsifier (i.e., nonionic such as polyoxyethylene sorbitan monostearate (TWEEN 60), anionic such as sodium oleate, zwitterionic such as lecithins) from about 0.01 weight % to about 25 weight %, and preferably from about 5 weight % to about 10 weight % can be included. Optionally, humectant (i.e., polyhydric alcohols such as glycerin, propylene glycol, maltitol, alkoxylated nonionic polymers such as polyethylene glycols, polypropylene glycols, etc.) from about 0.01 weight % to about 25 weight %, and preferably from about 1 weight % to about 5 weight % can be included. Viscosity control agents (i.e., suspending agents), which may be polymeric or colloidal (e.g., modified cellulose polymers such as methylcellulose, hydoxyethylcellulose, hydrophobically modified hydroxyethylcellulose, cross-linked acrylate polymers such as Carbomer, hydrophobically modified polyethers, and the like) from about 0.01 weight % to about 25 weight %, and preferably from about 0.5 weight % to about 10 weight % can be included. Optionally, silicas which may be hydrophobic (i.e., silanol surface treated with halogen silanes, alkoxysilanes, silazanes, siloxanes, etc. such as SIPERNAT D17, AEROSIL R972 and R974 (available from Degussa), etc.) and/or hydrophilic such as AEROSIL 200, SIPERNAT 22S, SIPERNAT 50S, (available from Degussa), SYLOID 244 (available from Grace Davison), etc., from about 0.01 weight % to about 20 weight %, and preferable from about 0.5 weight % to about 5 weight % can be included.

Further suitable humectants and viscosity control/suspending agents are disclosed in U.S. Pat. Nos. 4,428,869, 4,464,271, 4,446,032, and 6,930,078. Details of hydrophobic silicas as a functional delivery vehicle of active materials other than a free flow/anticaking agent are disclosed in U.S. Pat. Nos. 5,500,223 and 6,608,017.

In accordance with other embodiments, the two or more different types of capsules of the system have been cured in a different manner, e.g., different cure temperatures, different heating rates and/or different curing times. By way of illustration, a first capsule can be cured at a temperature of 125° C. and a second capsule can be cured at 85° C. so that the first and second capsules have been cured at different temperatures. In another illustrative example, a first capsule can be cured at 90° C. for 2 hours and a second capsule can be cured for 4 hours so that the first and second capsules have been cured for different times.

According to one embodiment of the invention, there is a direct relationship between higher cure temperature and less leaching of active material from the microcapsule. In accordance with this embodiment, the retention capabilities of a microcapsule are improved when the crosslinked network of polymers containing active materials are cured at temperatures at or above 100° C. In a preferred embodiment, the retention capabilities of one microcapsule in the capsule delivery system are improved when the cure temperature is above 110° C. In a more preferred embodiment, the retention capabilities of this microcapsule are improved when the cure temperature is above 120° C.

To obtain a microcapsule with more leaching of the active material from the microcapsule, certain embodiments of this invention provide for a cure temperature of less than 100° C. In some embodiments, the cure temperature of a microcapsule is at or less than 90° C. (e.g., about 50 to about 90° C.). In other embodiments, the cure temperature of a microcapsule is at or less than 80° C. (e.g., about 50 to about 70° C.).

In particular embodiments, a first capsule is cured at a temperature at or above 100° C. and a second capsule is cured at a temperature below 100° C. In other embodiments, a first capsule is cured at a temperature above 120° C. and a second capsule is cured at a temperature of between about 75 and 99° C.

Furthermore, higher performance of the microcapsules can be achieved by curing at a higher temperature for a longer time. Therefore, in some embodiments, the crosslinked network of polymers containing active materials may be cured for periods of up to 1 hour and more preferably longer than two hours. More preferably, the curing period of the capsule is at least up to about 2 hours, at least up to about 3 hours or at least up to about 4 hours. In particular embodiments, a first capsule is cured between about 1 and about 4 hours and a second capsule is cured between about 1 and about 4 hours. In certain embodiments, both the first and second capsules are cured for about 1 to about 3 hours at different temperatures.

In a more preferred embodiment, greater performance of the microcapsules can be achieved when the heating profile to the target cure temperature of the crosslinked network of polymers containing the active material is preferably linear with a heating rate at least up to about 2° C. a minute, preferably at least up to about 5° C. a minute, more preferably at least up to about 8° C. a minute and even more preferably at least up to about 10° C. a minute over a period of time less than about sixty minutes and more preferably less than about thirty minutes. The following heating methods may be used in the practice of the present invention, conduction for example via oil, steam radiation via infrared, and microwave, convection via heated air, steam injection and other methods known by those skilled in the art.

According the present invention, the target cure temperature is the minimum temperature in degrees Celsius at which the capsule comprising crosslinked network of polymers containing active materials may be cured for a period of minimal time period to retard leaching. The time period at the target cure temperature needed to retard leaching can be from at least up to about two minutes to at least up to about 1 hour before the capsules are cooled. More preferably, the curing period of the capsule is at least up to about 2 hours, at least up to about 3 hours, or at least up to about 4 hours.

In a preferred embodiment, the combination of two or more types of microcapsules retain greater than about 40% of the encapsulated active material after a four week period in a consumer product, e.g., a base containing surfactants, alcohols, or volatile silicones that can leach active materials from capsules over time. In a more preferred embodiment, the microcapsules retain greater than about 50% of the encapsulated active material after a four week period. In a most preferred embodiment, the microcapsules retain greater than about 60% of the encapsulated active material. Retention capabilities may vary dependent on the formulation of the product base, such as the level of surfactant which may range from about 1% to about 50% as well as the nature of the encapsulated active material and storage temperature.

Leaching of active material, such as fragrance, occurs not only when stored in the consumer products but also when using detergents, fabric softener and other fabric care products during the wash and rinse cycle during washing. The microcapsules of the present invention also exhibit enhanced stability during the wash and rinse cycles.

The term high stability refers to the ability of a microcapsule product to retain for a period of time (e.g., 4 weeks and 8 weeks) at least 50 weight % of active materials in bases that have a tendency to promote leaching of the active material out of the microcapsule product into the base. As used herein stability of the products is measured at room temperature or above over a period of at least a week. Preferably the capsules of the present invention are allowed to be stored at 37° C. for more than about two weeks and preferably more than about four weeks. More particularly, a capsule is preferably stored for 8 weeks at 37° C., which represent a 6- to 12-month shelf-life of a consumer product.

The system of the present invention generally contains greater than about 10 weight % water, preferably greater than about 30 weight % water and more preferably greater than about 50 weight % water. In a further embodiment the system containing the combination of two or more types of microcapsules may be spray dried according to the process described in US 2007/0078071.

Well known materials such as solvents, surfactants, emulsifiers, and the like can be used in addition to the polymers described throughout the invention to encapsulate the active materials such as fragrance without departing from the scope of the present invention. It is understood that the term encapsulated is meant to mean that the active material is substantially covered in its entirety. Encapsulation can provide pore vacancies or interstitial openings depending on the encapsulation techniques employed. More preferably the entire active material portion of the present invention is encapsulated.

According to the invention, the combination of two or more types of microcapsules described herein is incorporated into consumer products. In some embodiments, the combination of two or more types of microcapsules is provided in a consumer product at a level of about 0.1 to about 10% by the total weight of the final consumer product. There are tremendous benefits for using the disclosed combination including providing high stability microcapsules, a longer shelf life, more stability during transportation and importantly superior sensory performance over time, e.g., a linear release profile.

It is believed that there exists a relationship between higher concentration of surfactants in the base of consumer products and an increased leaching effect of the encapsulated active materials out of the microcapsules and into the base. Bases that are primarily non-aqueous in nature, e.g., those that are based on alcohols, or volatile silicones can also leach active materials from capsules over time. Volatile silicones such as but not limited to cyclomethicone and are exemplified by SF1256 CYCLOPENTASILOXANE and SF1257 CYCLOPENTASILOXANE (General Electric Company). Volatile silicones are in a number of personal care products, such as antiperspirants, deodorants, hair sprays, cleansing creams, skin creams, lotions and stick products, bath oils, suntan and shaving product, make-up and nail polishes. In these product types, the base solvent itself solubilizes the active material.

According to the present invention, the system is well suited for a variety of applications, including wash-off products. In some embodiments, the system provides a first capsule and a second capsule at a ratio of about 1:9 to about 9:1, preferably about 1:2 to about 2:1. In particular embodiments, the system provides a first capsule and a second capsule at a ratio of about 1:1.

Wash-off products are understood to be those products that are applied for a given period of time and then are removed. These products are common in areas such as laundry products, and include detergents, fabric conditioners, and the like; as well as personal care products which include shampoos, conditioner, hair colors and dyes, hair rinses, body washes, soaps and the like.

As described herein, the present system is well suited for use in a variety of well-known consumer products such as laundry detergent and fabric softeners, liquid dish detergents, automatic dish detergents, as well as hair shampoos and conditioners. These products employ surfactant and emulsifying systems that are well known. By way of illustration, the consumer product can include between about 1 and about 75 weight % (e.g., about 1 and about 40 weight %) surfactant or emulsifier, or more preferably between 10 and 30 weight % surfactant or emulsifier. A fabric softener contains about 1 to about 40 weight % (e.g., about 1 to about 30 weight % and about 5 to about 20 weight %) fabric softening active. For example, fabric softener systems are described in U.S. Pat. Nos. 6,335,315, 5,674,832, 5,759,990, 5,877,145, 5,574,179; 5,562,849, 5,545,350, 5,545,340, 5,411,671, 5,403,499, 5,288,417, and 4,767,547, 4,424,134. Liquid dish detergents are described in U.S. Pat. Nos. 6,069,122 and 5,990,065; automatic dish detergent products are described in U.S. Pat. Nos. 6,020,294, 6,017,871, 5,968,881, 5,962,386, 5,939,373, 5,914,307, 5,902,781, 5,705,464, 5,703,034, 5,703,030, 5,679,630, 5,597,936, 5,581,005, 5,559,261, 4,515,705, 5,169,552, and 4,714,562. Liquid laundry detergents which can use the present invention include those systems described in U.S. Pat. Nos. 5,929,022, 5,916,862, 5,731,278, 5,565,145, 5,470,507, 5,466,802, 5,460,752, 5,458,810, 5,458,809, 5,288,431, 5,194,639, 4,968,451, 4,597,898, 4,561,998, 4,550,862, 4,537,707, 4,537,706, 4,515,705, 4,446,042, and 4,318,818. Shampoo and conditioners that can employ the present invention include those described in U.S. Pat. Nos. 6,162,423, 5,968,286, 5,935,561, 5,932,203, 5,837,661, 5,776,443, 5,756,436, 5,661,118, 5,618,523, 5,275,755, 5,085,857, 4,673,568, 4,387,090 and 4,705,681.

The invention will be further described in the following examples, which do not limit the scope of the invention described in the claims.

Example 1: Preparation of High Stability Fragrance-Containing Microcapsules

Fragrance was admixed with NEOBEE-M5 and 40% ethylene urea solution thereby forming a fragrance/solvent composition (Table 2). The uncoated capsules were prepared by creating a polymeric wall to encapsulate the fragrance/solvent composition droplets. To make the capsule slurry, a co-polyacrylamide/acrylate (ALCAPSOL 200) was dispersed in water together with a high imino methylated melamine crosslinker (CYMEL 385, Cytec Industries, Belgium) (Table 2). The capsule components were allowed to react under acidic conditions. The fragrance/solvent composition was then added into the solution and droplets of the desired size were achieved by high shear homogenization.

Twelve different capsules were produced. Capsules 1-10, which differed in the fragrance composition (Table 2) and the curing temperature/time as shown in the table.

Capsules 11 and 12 were prepared following the procedures described in Example 3 of U.S. Pat. No. 8,299,011 except that different fragrances were used.

TABLE 2

| Capsule | Capsule wall (wt %) | Fragrance | Curing temp (° C.)/time (hours) | Core Component (wt %) |
|---|---|---|---|---|
| 1 | ALCAPSOL 200: 5.7% CYMEL 385: 3.1% | Jillz | 125/1 | Fragrance: 28% Neobee-M5: 7% 40% ethylene urea solution: 5.7% |
| 2 | ALCAPSOL 200: 5.7% CYMEL 385: 3.1% | Greenfields | 80/1 | Fragrance: 28% Neobee-M5: 7% 40% ethylene urea solution: 5.7% |
| 3 | ALCAPSOL 200: 5.7% CYMEL 385: 3.1% | Jillz | 80/1 | Fragrance: 28% Neobee-M5: 7% 40% ethylene urea solution: 5.7% |
| 4 | ALCAPSOL 200: 5.7% CYMEL 385: 3.1% | Unicap 489 | 90/1 | Fragrance: 28% Mineral oil: 7% 40% ethylene urea solution: 5.7% |

TABLE 2-continued

| Capsule | Capsule wall (wt %) | Fragrance | Curing temp (° C.)/time (hours) | Core Component (wt %) |
|---|---|---|---|---|
| 5 | ALCAPSOL 200: 5.7% CYMEL 385: 3.1% | Unicap 101 | 90/1 | Fragrance: 28% Mineral oil: 7% 40% urea liquor solution: 6.6% |
| 6 | ALCAPSOL 200: 5.7% CYMEL 385: 3.1% | Fresh Response | 90/3 | Fragrance: 30% Mineral oil: 7% 40% urea liquor solution: 6.6% |
| 7 | ALCAPSOL 200: 5.7% CYMEL 385: 3.1% | Jillz | 90/3 | Fragrance: 45% 40% ethylene urea solution: 5.7% |
| 8 | ALCAPSOL 200: 5.7% CYMEL 385: 3.1% | Eden | 80/1 | Fragrance: 28% Neobee-M5: 7% 40% ethylene urea solution: 5.7% |
| 9 | ALCAPSOL 200: 5.7% CYMEL 385: 3.1% | Express Cap | 80/1 | Fragrance: 28% Neobee-M5: 7% 40% ethylene urea solution: 5.7% |
| 10 | ALCAPSOL 200: 5.7% CYMEL 385: 3.1% | Express Cap | 80/1 | Fragrance: 28% Neobee-M5: 7% 40% ethylene urea solution: 5.7% |
| 11 | Polyurea | LL Cloud | 55/2 | Fragrance: 32 wt % Neobee-M5: 8 wt % |
| 12 | Polyurea | Fruity Bomb | 55/2 | Fragrance: 32 wt % Neobee-M5: 8 wt % |

All fragrance commercially available from International Flavors & Fragrances Inc.

TABLE 3

| Fragrance | Oil with High saturated vapor pressure at 23° C. (>0.01 mmHg) [wt %] | Oil with Low Saturated vapor pressure at 23° C. (<0.01 mmHg) [wt %] |
|---|---|---|
| Jillz | 81% | 18% |
| Greenfields | 53% | 46% |
| Unicap 489 | 59% | 41% |
| Unicap 101 | 53% | 47% |
| Fresh Response | 53% | 47% |
| Eden | 61% | 39% |
| Express Cap | 65% | 35% |
| LL Cloud | 78% | 22% |
| Fruity Bomb | 67% | 33% |

Example 2: Preparation of Fabric Softener Samples Containing Capsules

In this example, an unfragranced model fabric conditioner containing approximately 20% cationic quaternary surfactants was used. Nine samples and ten comparative samples were prepared following the procedures described below.

In Sample 1 and Comparative 1 and 1', both Capsules 1 and 2 having shell walls composed of an acrylamide-acrylic acid co-polymer cross linked with melamine-formaldehyde resin as described in Example 1 were mixed with the model fabric conditioner separately or at a ratio shown in Table 4 below. The resultant mixture was stirred using an overhead agitator at 300 rpm until homogeneous.

TABLE 4

| Softener | Capsule 1 (wt %) | Capsule 2 (wt %) |
|---|---|---|
| Comparative 1 | 0.9 | 0 |
| Sample 1 | 0.6 | 0.3 |
| Comparative 1' | 0 | 0.9 |

The fabric softener samples were stored at 5° C. or 37° C. for 4, 6 and 8 weeks. Historical data shows that samples stored at 5° C. perform equal to samples that are freshly prepared.

Example 3: Sensory Performance of Microcapsules in Model Fabric Conditioner

The fabric conditioner samples (20 grams per sample) prepared in Example 2 were introduced into a Miele Professional PW6055 Plus front loader washing machine during the rinse cycle thereof to condition eight hand towels, in total weighing approximately 2200 gm including bulk load. After rinsing, the damp towels were evaluated by a sensory panel of 16 people using the Label Magnitude Scale (LMS) from 0 to 99, wherein 3="barely detectable", 7="weak", 16="moderate and 32="strong". Sensory scores were recorded. A set of eight towels from a second wash were lined dried for 24 hours followed by sensory evaluation of the eight towels. The eight selected dry towels were thus evaluated by a panel of 16 people using the LMS.

Sensory scores were recorded before and after each of the eight randomly selected towels contained in a separate polyethylene bag were rubbed by hand. Each rubbing test including rubbing the towels five times, 2 seconds per time interval, for a total rubbing time of 10 seconds. The absolute intensity scores were obtained from the sensory panel. See Table 5 below. Comparing to the scores for samples stored at 5° C./4 weeks, which perform equal to samples that are freshly prepared, the changes of scores were calculated as (Score for sample stored at 37° C.−Score for sample stored at 5° C.)/Score for sample stored at 5° C.×100%. The percentages of changes were shown in Table 6 below. A positive percentage indicates that the score was increased and a negative percentage indicates that the score was decreased.

As compared to the samples obtained after 4 weeks at 5° C., at all three stages (damp, pre-rub, and post-rub), both Comparative 1 (containing only Capsule 1) and Comparative 1' (containing only Capsule 2) had significant changes.

Unexpectedly, Sample 1 of this invention showed much less changes at damp when stored at 37° C. for 4 weeks or 8 weeks. Further, this sample gave a constant linear release profile across extended storage conditions, as compared to that of either Comparative 1 or 1'.

TABLE 5

| Conditioner | 5° C. (4 weeks) | | | 37° C. (4 weeks) | | | 37° C. (8 weeks) | | |
|---|---|---|---|---|---|---|---|---|---|
| | Damp | Pre-Rub | Post-Rub | Damp | Pre-Rub | Post-Rub | Damp | Pre-Rub | Post-Rub |
| Comparative 1' | 15.4 | 13.7 | 17.0 | 16.8 | 9.7 | 10.2 | 16.7 | 8.1 | 7.9 |
| Sample 1 | 13.9 | 12.5 | 20.6 | 13.4 | 10.3 | 18.5 | 13.7 | 8.9 | 15.3 |
| Comparative 1 | 12.9 | 8.4 | 25.3 | 14.5 | 13.9 | 22.7 | 19.0 | 9.2 | 18.7 |

TABLE 6

| Conditioner | 37° C. (4 weeks) | | | 37° C. (8 weeks) | | |
|---|---|---|---|---|---|---|
| | Damp | Pre-Rub | Post-Rub | Damp | Pre-Rub | Post-Rub |
| Comparative 1 | 12.4% | 65.5% | −10.3% | 47.3% | 9.5% | −26.1% |
| Sample 1 | −3.6% | −17.6% | −10.2% | −1.4% | −28.8% | −25.7% |
| Comparative 1' | 9.1% | −29.2% | −40% | 8.4% | −40.9% | −53.5% |

Example 4: Delivery Systems Containing Neat Fragrance Oil

Also prepared are eight samples (2-9) of this invention and eight comparatives (2'-9'), each containing a neat fragrance oil.

Five fabric conditioners, i.e., Samples 2-4, 8, and 9, each were obtained using the method described in Example 2 above except that a neat fragrance oil and two different capsules were used at percentages as described in Table 9 below. Comparative 2'-4', 8', and 9' were prepared in exactly the same manner except that a single capsule, instead of two capsules, was used.

TABLE 9

| Sample | Format | NEAT OIL wt % | CAP 4 [% NOE] | CAP 5 [% NOE] | CAP 6 [% NOE] |
|---|---|---|---|---|---|
| 2 | Fabric Conditioner | 0.85 | 0.19 | 0 | 0.1 |
| 2' | Fabric Conditioner | 0.85 | 0.19 | 0 | 0 |
| 3 | Fabric Conditioner | 0.86 | 0.19 | 0 | 0.1 |
| 3' | Fabric Conditioner | 0.86 | 0.19 | 0 | 0 |
| 4 | Fabric Conditioner | 0.93 | 0.22 | 0 | 0.1 |
| 4' | Fabric Conditioner | 0.93 | 0.22 | 0 | 0 |
| 5 | Detergent Powder | 0.36 | 0.26 | 0 | 0.1 |
| 5' | Detergent Powder | 0.36 | 0.26 | 0 | 0 |
| 6 | Detergent Powder | 0.49 | 0 | 0.1 | 0.1 |
| 6' | Detergent Powder | 0.49 | 0 | 0.1 | 0 |
| 7 | Detergent Powder | 0.54 | 0.1 | 0 | 0.1 |
| 7' | Detergent Powder | 0.54 | 0.1 | 0 | 0 |
| 8 | Fabric Conditioner | 0.91 | 0.15 | 0 | 0.1 |
| 8' | Fabric Conditioner | 0.91 | 0.15 | 0 | 0 |
| 9 | Fabric Conditioner | 0.91 | 0 | 0.22 | 0.1 |
| 9' | Fabric Conditioner | 0.91 | 0 | 0.22 | 0 |

The performance of these ten fabric conditioners was evaluated. More specifically, the fabric conditioner samples (35 grams per sample) each were separately introduced into a Miele Professional PW6055 Plus front loader washing machine during the rinse cycle thereof to condition a 3 hand towels total weighing of wash load approximately 2200 grams including bulk load. After rinsing, one of the damp towels was evaluated blind by a panel of 3 people on intensity. A set 3 towels from a second wash, using the same wash conditions immediately above were lined dried for 24 hours. The 3 dry towels each were stored in a polyethylene bag and evaluated by a panel of 3 people. Scores were recorded before and after each of the towels was rubbed by hand. Each rubbing test employed 5 times intervals, 2 seconds per time interval for a total rubbing time of 10 seconds. One of the following five performances was assigned to each sample at Point of Purchase (hereinafter "POP"), damp, and dry post-rub: (i) hardly any performance, (ii) weak performance, (iii) good performance, (iv) very good performance, and (vi) excellent good performance.

Unexpectedly, fabric conditioner Samples 2-4, 8, and 9 each had a reasonable performance at POP and damp and a good to very good performance at dry post-rub. By contrast, Comparatives 2'-4', 8', and 9' each received a score of "hardly any performance" at POP, damp and dry post rub.

Similarly, three detergent power samples (Samples 5-7) of this invention and three comparatives (5'-7') were prepared and evaluated following the procedures described below.

To obtain Samples 5-7, a capsule slurry was first provided using a fragrance oil and two capsules selected from Capsules 4-6. See Table 9 above for the capsules and their ratio in each sample. The slurry was added dropwise to an un-fragranced model powder detergent machine wash base. The resultant mixture was allowed to dry overnight. Comparatives 5'-7' were also prepared using a single capsule instead of two capsules.

To evaluate performance, 80 grams of a powder detergent sample or comparative was introduced into a Miele Professional PW6055 Plus front loader washing machine during the main wash cycle to wash 3 hand towels total weighing of wash load 2200 grams including bulk load. After rinsing, one damp towel was evaluated blind by a panel of 3 people on fragrance intensity. Three more towels were washed in the same manner and lined dried for 24 hours. The 3 dry towels each were stored in a polyethylene bag and evaluated by a panel of 3 people. Scores were recorded before and after each of the towels was rubbed by hand. Each rubbing test employed 5 times intervals, 2 seconds per time interval for a total rubbing time of 10 seconds. One of the following five performances was assigned to each sample at POP, damp, and dry post-rub: (i) hardly any performance, (ii) weak performance, (iii) good performance, (iv) very good performance, and (vi) excellent performance.

Unexpectedly, detergent powder Samples 5-7 each had a good performance at POP, damp and dry post-rub as compared to comparative examples, which each received a score of "hardly any performance" at these three stages.

Example 5: Delivery Systems and Malodor Counteractant Performance

Two delivery systems of this invention were prepared and evaluated for malodor reduction performance.

More specifically, Fabric conditioner Samples 10 and 11 were obtained using the procedure described in Example 4 above with neat fragrance oil Blue Energy (commercially available from International Flavors and Fragrances), and Capsules 4 and 6 (prepared in Example 1). The ratios of the components are shown in Table 10 below. Note that Fragrance Blue Energy does not contain a malodor counteractant and the fragrance encapsulated in Capsule 6, contains a malodor counteractant.

TABLE 10

| Fabric Conditioner | Delivery System | | |
|---|---|---|---|
| | Blue Energy, wt % | Capsule 4, wt % NOE | Capsule 6, wt % NOE |
| Sample 10 | 0.93 | 0.22 | 0.1 |
| Sample 11 | 0.93 | 0.19 | 0.1 |

To evaluate malodor reduction performance of Samples 10 and 11, sweat malodor (0.25-0.3 grams) was sprayed on a terry towel (36 grams). Multiple towels were used. These towels were stored in a large capped beaker and left for 16 hours. Controls, i.e., untreated terry towels were also kept for 16 hours in a closed beaker.

In a handwash application, the terry towels were rinsed with Samples 10 and 11 at a concentration of 2.5 grams/L in water at 20° C. In a liter of water containing a sample, two terry towels were added and allowed to stay for 10 minutes. The towels were then taken out and passed through a wringer.

The terry towels were evaluated on damp as well as on dry before and after rubbing by 6 trained panelists for malodor intensity. The results showed that Samples 10 and 11 significantly reduced malodors on damp, pre-rub dry and post-rub dry.

Example 6: Delivery System and its Release Profile

Following the procedure described in Example 4, a fabric conditioner, i.e., Sample 12, was prepared, as well as Comparatives 12 and 12'. Sample 12 contained 0.5 wt % (Neat Oil Equivalence) of Fragrance Jillz encapsulated a delivery system of this invention, i.e., a combination of Capsules 2 and 7, Comparative 12 contained 0.5 wt % (NOE) of Jillz encapsulated in Capsule 2, and Comparative 12' contained 0.5 wt % (NOE) of Jillz encapsulated in Capsule 7.

These fabric conditioners were then evaluated right after being prepared and after being stored at 37° C. for 4 weeks. More specifically, a fabric conditioner (100 grams of Sample 12, Comparative 12, or Comparative 12') was introduced into a US top loader washing machine during the rinse cycle to condition 8 hand towels with a total wash load of 2200 grams including bulk load. After being rinsed, the damp towels were evaluated by a sensory panel of 16 people using the Label Magnitude Scale (LMS) from 0 to 99, wherein 3="barely detectable", 7="weak", 16="moderate, and 32="strong". Sensory scores were recorded. Another set of eight towels from a second wash were heat dried and then evaluated in the same manner before and after rubbing. Sensory scores were recorded and summarized in Table 11 below.

TABLE 11

| Fabric Softener | Freshly Prepared | | | 37° C. (4 weeks) | | |
|---|---|---|---|---|---|---|
| | Damp | Pre-Rub | Post-Rub | Damp | Pre-Rub | Post-Rub |
| Comparative 12 | 8.3 | 3.8 | 10.8 | 11.2 | 7.2 | 12.2 |
| Sample 12 | 6 | 3.5 | 13.1 | 9.55 | 7.7 | 15.6 |
| Comparative 12' | 4.3 | 4.7 | 13 | 4.89 | 4.3 | 13.9 |

Comparative 12 gave a good score on damp and Comparative 12' gave a good score on post-rub dry. Unexpectedly, Sample 12 of this invention has a damp score higher than Comparative 12' and a dry postrub score higher than Comparative 12. Thus, Sample 12 gives a more balanced release profile when freshly prepared or stored at 37° C. for 4 weeks.

Example 7: Delivery Systems Containing a Polyurea Capsule

Capsules 11 and 12 each have a polyurea capsule wall. See Example 1 above. Following the procedure described in Example 4, two fabric conditioners, i.e., Sample 13 and 14, were prepared, along with Comparatives 13, 13', and 14. All fabric conditioners contained neat fragrance oil Blue Energy.

Sample 13 was formed of Capsule 8 (0.15 wt % NOE) and Capsule 11 (0.45 wt % NOE). See Table 12 below. Comparatives 13 and 13' each contained Capsule 11 and a different amount of neat oil.

TABLE 12

| Fabric Conditioner | Blue Energy (wt %) | Capsule 8 (wt % NOE) | Capsule 11 (wt % NOE) |
|---|---|---|---|
| Comparative 13 | 0.76 | 0 | 0.31 |
| Comparative 13' | 0.3 | 0 | 0.6 |
| Sample 13 | 0.3 | 0.15 | 0.45 |

Sample 13 and the two comparatives were evaluated following the same procedure described in Example 6 above. The scores were recorded and the changes were calculated as shown in Table 13 below.

TABLE 13

| Fabric Conditioner | Initial | | 4 weeks 37° C. | | | |
|---|---|---|---|---|---|---|
| | Pre-Rub | Post-Rub | Pre-Rub | Change | Post-Rub | Change |
| Comparative 13 | 13.8 | 17.6 | 6.8 | 50.7% | 13.4 | 23.9% |
| Comparative 13' | 15 | 20.1 | 7.8 | 48.0% | 14.1 | 29.9% |
| Sample 13 | 14.5 | 19.6 | 9.7 | 33.1% | 16 | 18.4% |

Unexpectedly, fabric conditioner Sample 13 was more stable than Comparatives 13 and 13', evidenced by the less change of performance after stored at 37° C. for 4 weeks.

Sample 14 was formed of fragrance Blue Energy (0.16 wt %), Capsule 9 (0.07 wt % NOE), Capsule 10 (0.05 wt % NOE), and Capsule 12 (0.25 wt % NOE). Comparative 14 contained Blue Energy (0.7 wt %) and Capsule 12 (0.12 wt % NOE).

Sample 14 and Comparative 14 were evaluated following the same procedure described in Example 6. The scores are shown in Table 14 below.

TABLE 14

| Fabric | Freshly prepared | |
|---|---|---|
| Conditioner | Pre-Rub | Post-Rub |
| Comparative 14 | 19.8 | 25.4 |
| Sample 14 | 22.2 | 29.2 |

Sample 14, containing 3 capsules, had higher pre- and post-rub scores as compared to that of Comparative 14, containing only one capsule.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Indeed, to achieve the purpose of a capsule delivery system, one skilled in the art can use different capsules to achieve desirable organoleptic or release profiles in a consumable product. Further, the ratios among these capsules can also be determined by a skilled artisan through assays known in the art to prepare delivery systems with desirable properties.

From the above description, a skilled artisan can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A capsule delivery system comprising a first capsule containing a first capsule wall encapsulating a first active material and a second capsule containing a second capsule wall encapsulating a second active material, wherein the first capsule wall is formed of melamine-formaldehyde, the second capsule wall is formed of polyurea, the first active material is a first fragrance, the second active material is a second fragrance, and the first fragrance and second fragrances are different.

2. The capsule delivery system of claim 1, wherein the melamine-formaldehyde of the first capsule wall is formed from co-polyacrylamide/acrylate and methylated melamine crosslinker.

3. The capsule delivery system of claim 1, wherein the first capsule is cured at or above about 70° C. for about 0.5 to about 5 hours, the second capsule is cured at or above about 50° C. for about 0.5 to 5 hours.

4. The capsule delivery system of claim 1, further comprising a starch particle that contains an active material.

5. The capsule delivery system of claim 1, wherein
the first capsule
(i) contains the first fragrance having a plurality of fragrance ingredients, about 50 to 100 weight % of which have a saturated vapor pressure at 23° C. of about 0.01 mm Hg or greater, and
(ii) is cured at a temperature at about 70 to about 130° C. for about 0.5 to about 2 hours; and
the second capsule
(i) contains the second fragrance having a plurality of fragrance ingredients, about 20 to 100 weight % of which have a saturated vapor pressure at 23° C. of about 0.01 mm Hg or greater, and
(ii) is cured at a temperature of about 50 to about 110° C. for about 0.5 to about 2 hours.

6. The capsule delivery system of claim 1, wherein the first and second capsules are present in a ratio of about 1:9 to about 9:1.

7. The capsule delivery system of claim 1, wherein the first or second capsule further comprises a malodor counteractant.

8. The capsule delivery system of claim 7, wherein the malodor counteractant is 1-cyclohexylethan-1-yl butyrate, 1-cyclohexylethan-1-yl acetate, 1-cyclohexylethan-1-ol, 1-(4'-methylethyl)cyclohexylethan-1-yl propionate, 2'-hydroxy-1'-ethyl(2-phenoxy)acetate, or a combination thereof.

9. The capsule delivery system of claim 1, wherein the first and second capsules are stable for four weeks or longer when added to a consumer product base and stored at about 37° C., the consumer product being a fabric conditioner, detergent, fabric spray, personal wash product, home care product, liquid soap, or hair care product.

10. The capsule delivery system of claim 1, further comprising a third capsule, a fourth capsule, a fifth capsule, a sixth capsule, or a seventh capsule.

11. The capsule delivery system of claim 1, wherein the polyurea of the second capsule wall is formed from one or more multi-functional isocyanates and one or more multi-functional amines.

12. The capsule delivery system of claim 11, wherein the one or more multifunctional isocyanates are selected from the group consisting of 1,5-naphthylene diisocyanate, 4,4'-diphenylmethane diisocyanate, hydrogenated MDI, xylylene diisocyanate, tetramethylxylol diisocyanate, 4,4'-diphenyldimethylmethane diisocyanate, di- or tetra-alkyldiphenylmethane diisocyanate, 4,4'-dibenzyl diisocyanate, 1,3-phenylene diisocyanate, 1,4-phenylene diisocyanate, the isomers of tolylene diisocyanate, 1-methyl-2,4-diisocyanatocyclohexane, 1,6-diisocyanato-2,2,4-trimethylhexane, 1,6-diisocyanato-2,4,4-trimethylhexane, 1-isocyanatomethyl-3-isocyanato-1,5,5-trimethylcyclohexane, chlorinated and brominated diisocyanates, phosphorus-containing diisocyanates, 4,4'-diisocyanatophenylperfluoroethane, tetramethoxybutane 1,4-diisocyanate, butane 1,4-diisocyanate, hexane 1,6-diisocyanate, dicyclohexylmethane diisocyanate, cyclohexane 1,4-diisocyanate, ethylene diisocyanate, phthalic acid bisisocyanatoethyl ester, 1-chloromethylphenyl 2,4-diisocyanate, 1-bromomethylphenyl 2,6-diisocyanate, 3,3-bischloromethyl ether 4,4'-diphenyldiisocyanate, hexamethylene diisocyanate, trimethylhexamethylene diisocyanate, 1,4-diisocyanatobutane, 1,2-diisocyanatododecane, and dimer fatty acid diisocyanate.

13. The capsule delivery system of claim 11, wherein the one or more multifunctional amines are selected from the group consisting of methylenediamine, ethylenediamine, 1,3-diaminopropane, 1,4-diaminobutane, hexaethylene diamine, hexamethylene diamine, pentaethylenehexamine, polyalykylene polyamine, diethylene triamine, triethylene tetraamine, bis(3-aminopropyl)amine, bis(hexamethylene) triamine, polyetheramine, 2,2'-ethylenedioxy)bis(ethylamine), 4,7,10-trioxa-1,13-tridecanediamine, tris(2-aminoethyl)amine, triethylenetetramine, N,N'-bis(3-aminopropyl)-1,3-propanediamine, tetraethylene pentamine, 1,2-diaminopropane, N,N,N',N'-tetrakis(2-hydroxyethyl)ethylene diamine, N,N,N',N'-tetrakis(2-hydroxypropyl)ethylene diamine, branched polyethylenimine, 2,4-diamino-6-hydroxypyrimidine, 2,4,6-triaminopyrimidine, gelatin, L-lysine, L-arginine, L-lysine monohydrochloride, arginine monohydrochloride, ornithine monohydrochloride, a guanidine amine, a guanidine salt, 1,3-diaminoguanidine monohydrochloride, 1,1-dimethylbiguanide hydrochloride, guanidine carbonate, and guanidine hydrochloride.

14. The capsule delivery system of claim 11, wherein the one or more multifunctional isocyanates are selected from the group consisting of 4,4'-diphenylmethane diisocyanate, xylylene diisocyanate, and hexamethylene diisocyanate, and the one or more multifunctional amines are selected from the group consisting of hexamethylene diamine, branched polyethylenimine, a guanidine amine, and a guanidine salt.

15. A consumer product comprising a capsule delivery system of claim 1.

16. The consumer product of claim 15, wherein the consumer product is a fabric conditioner, detergent, fabric spray, personal wash product, home care product, liquid soap, shampoo, rinse-off conditioner, or leave-on conditioner.

17. The consumer product of claim 15, wherein the consumer product is a fabric conditioner or detergent, the fabric conditioner contains about 1 to about 30 weight % of a fabric conditioning active, and the detergent contains about 1 to about 75 weight % of detergent surfactant.

18. The consumer product of claim 17, wherein the consumer product is a fabric conditioner containing about 5 to about 10 weight % of a fabric conditioning active.

19. The consumer product of claim of claim 17, wherein the consumer product is a fabric conditioner containing about 8 to about 15 weight % of a fabric conditioning active.

* * * * *